(12) United States Patent
Mi et al.

(10) Patent No.: US 8,301,262 B2
(45) Date of Patent: Oct. 30, 2012

(54) DIRECT INDUCTIVE/ACOUSTIC CONVERTER FOR IMPLANTABLE MEDICAL DEVICE

(75) Inventors: Bin Mi, Plymouth, MN (US); Abhijeet V. Chavan, Maple Grove, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 499 days.

(21) Appl. No.: 12/357,460

(22) Filed: Jan. 22, 2009

(65) Prior Publication Data

US 2009/0198307 A1  Aug. 6, 2009

Related U.S. Application Data

(60) Provisional application No. 61/026,607, filed on Feb. 6, 2008.

(51) Int. Cl.
*A61N 1/00* (2006.01)
(52) U.S. Cl. ............... 607/60; 607/30; 607/32
(58) Field of Classification Search .......... 607/30, 607/32, 60
See application file for complete search history.

(56) References Cited

U.S. PATENT DOCUMENTS

| | | | |
|---|---|---|---|
| 3,672,352 A | 6/1972 | Summers | |
| 4,361,153 A | 11/1982 | Slocum et al. | |
| 4,373,527 A | 2/1983 | Fischell | |
| 4,481,950 A | 11/1984 | Duggan | |
| 4,519,401 A | 5/1985 | Ko et al. | |
| 4,573,994 A | 3/1986 | Fischell et al. | |
| 4,614,192 A | 9/1986 | Imran et al. | |
| 4,616,640 A | 10/1986 | Kaali et al. | |
| 4,651,740 A | 3/1987 | Schroeppel | |
| 4,793,825 A | 12/1988 | Benjamin et al. | |
| 5,113,859 A | 5/1992 | Funke | |
| 5,423,334 A | 6/1995 | Jordan | |
| 5,713,939 A * | 2/1998 | Nedungadi et al. | 607/33 |
| 5,733,313 A * | 3/1998 | Barreras et al. | 607/33 |
| 5,778,882 A | 7/1998 | Raymond et al. | |
| 5,800,478 A | 9/1998 | Chen et al. | |
| 5,814,089 A | 9/1998 | Stokes et al. | |
| 5,833,603 A | 11/1998 | Kovacs et al. | |
| 6,140,740 A | 10/2000 | Porat et al. | |
| 6,141,588 A | 10/2000 | Cox et al. | |
| 6,162,238 A | 12/2000 | Kaplan et al. | |
| 6,164,284 A | 12/2000 | Schulman et al. | |

(Continued)

FOREIGN PATENT DOCUMENTS
EP  0300552  1/1989
(Continued)

OTHER PUBLICATIONS

U.S. Appl. No. 12/122,431, filed May 16, 2008.

*Primary Examiner* — Niketa Patel
*Assistant Examiner* — William Levicky
(74) *Attorney, Agent, or Firm* — Faegre Baker Daniels LLP (57) ABSTRACT

Systems and methods for communicating with or powering implantable medical devices using a direct inductive/acoustic telemetry link are disclosed. An illustrative system includes an interrogator device located outside of the patient's body, an implantable medical device including an energy translator circuit adapted to convert inductive or RF signals received from the interrogator device into an acoustic signal for driving an acoustic transducer, and a remote device adapted to sense one or more parameters within the body.

18 Claims, 10 Drawing Sheets

U.S. PATENT DOCUMENTS

| | | |
|---|---|---|
| 6,170,488 B1 | 1/2001 | Spillman, Jr. et al. |
| 6,185,452 B1 | 2/2001 | Schulman et al. |
| 6,200,265 B1 | 3/2001 | Walsh et al. |
| 6,234,973 B1 | 5/2001 | Meador et al. |
| 6,236,889 B1 | 5/2001 | Soykan et al. |
| 6,277,078 B1 | 8/2001 | Porat et al. |
| 6,308,099 B1 | 10/2001 | Fox et al. |
| 6,336,903 B1 | 1/2002 | Bardy |
| 6,368,284 B1 | 4/2002 | Bardy |
| 6,398,728 B1 | 6/2002 | Bardy |
| 6,411,840 B1 | 6/2002 | Bardy |
| 6,431,175 B1 | 8/2002 | Penner et al. |
| 6,440,066 B1 | 8/2002 | Bardy |
| 6,442,413 B1 | 8/2002 | Silver |
| 6,442,433 B1 | 8/2002 | Linberg |
| 6,445,953 B1 | 9/2002 | Bulkes et al. |
| 6,453,196 B1 | 9/2002 | Von Arx et al. |
| 6,456,602 B1 | 9/2002 | Hwang et al. |
| 6,456,883 B1 | 9/2002 | Torgerson et al. |
| 6,472,991 B1 | 10/2002 | Schulman et al. |
| 6,571,128 B2 | 5/2003 | Lebel et al. |
| 6,628,989 B1 | 9/2003 | Penner et al. |
| 6,638,231 B2 | 10/2003 | Govari et al. |
| 6,654,638 B1 | 11/2003 | Sweeney |
| 6,675,049 B2 | 1/2004 | Thompson et al. |
| 6,712,772 B2 | 3/2004 | Cohen et al. |
| 6,764,446 B2 | 7/2004 | Wolinsky et al. |
| 6,783,499 B2 | 8/2004 | Schwartz |
| 6,792,311 B2 | 9/2004 | Fox et al. |
| 6,809,507 B2 | 10/2004 | Morgan et al. |
| 6,823,031 B1 | 11/2004 | Tatem, Jr. |
| 6,840,956 B1 | 1/2005 | Wolinsky et al. |
| 6,855,115 B2 | 2/2005 | Fonseca et al. |
| 6,895,265 B2 | 5/2005 | Silver |
| 6,907,285 B2 | 6/2005 | Denker et al. |
| 6,978,182 B2 | 12/2005 | Mazar et al. |
| 6,985,773 B2 | 1/2006 | Von Arx et al. |
| 7,003,350 B2 | 2/2006 | Denker et al. |
| 7,018,336 B2 | 3/2006 | Enegren et al. |
| 7,024,248 B2 | 4/2006 | Penner et al. |
| 7,027,871 B2 | 4/2006 | Burnes et al. |
| 7,033,322 B2 | 4/2006 | Silver |
| 7,061,381 B2 | 6/2006 | Forcier et al. |
| 7,134,999 B2 | 11/2006 | Brauker et al. |
| 7,187,979 B2 | 3/2007 | Haubrich et al. |
| 7,198,603 B2 | 4/2007 | Penner et al. |
| 7,214,189 B2 | 5/2007 | Zdeblick |
| 7,236,821 B2 | 6/2007 | Cates et al. |
| 7,273,454 B2 | 9/2007 | Raymond et al. |
| 7,273,457 B2 | 9/2007 | Penner |
| 7,399,313 B2 | 7/2008 | Brown et al. |
| 7,425,200 B2 | 9/2008 | Brockway et al. |
| 7,452,334 B2 | 11/2008 | Gianchandani et al. |
| 7,481,771 B2 | 1/2009 | Fonseca et al. |
| 2001/0043514 A1 | 11/2001 | Kita |
| 2002/0042561 A1 | 4/2002 | Schulman et al. |
| 2002/0045812 A1 | 4/2002 | Ben-Haim et al. |
| 2002/0151770 A1 | 10/2002 | Noll, III et al. |
| 2002/0183628 A1 | 12/2002 | Reich et al. |
| 2003/0009204 A1 | 1/2003 | Amundson |
| 2003/0136417 A1 | 7/2003 | Fonseca et al. |
| 2003/0181794 A1 | 9/2003 | Rini et al. |
| 2003/0191383 A1 | 10/2003 | Ben-Haim et al. |
| 2003/0195581 A1* | 10/2003 | Meadows et al. ............... 607/29 |
| 2004/0057340 A1 | 3/2004 | Charles-Erickson et al. |
| 2004/0064133 A1 | 4/2004 | Miller et al. |
| 2004/0088009 A1 | 5/2004 | Degroot |
| 2004/0152999 A1 | 8/2004 | Cohen et al. |
| 2005/0056539 A1 | 3/2005 | Morgan et al. |
| 2005/0159789 A1 | 7/2005 | Brockway et al. |
| 2005/0187482 A1 | 8/2005 | O'Brien et al. |
| 2005/0215887 A1 | 9/2005 | Ben-Haim et al. |
| 2005/0242479 A1 | 11/2005 | Petisce et al. |
| 2006/0004263 A1 | 1/2006 | Feliss et al. |
| 2006/0009818 A1 | 1/2006 | Von Arx et al. |
| 2006/0030903 A1 | 2/2006 | Seeberger et al. |
| 2006/0031378 A1 | 2/2006 | Vallapureddy et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0122667 A1* | 6/2006 | Chavan et al. .................. 607/60 |
| 2006/0136004 A1 | 6/2006 | Cowan et al. |
| 2007/0053513 A1 | 3/2007 | Hoffberg |
| 2007/0142728 A1 | 6/2007 | Penner et al. |
| 2007/0208261 A1 | 9/2007 | Maniak et al. |
| 2008/0021333 A1 | 1/2008 | Huelskamp |
| 2008/0021972 A1 | 1/2008 | Huelskamp et al. |
| 2008/0082146 A1 | 4/2008 | Gandhi et al. |
| 2008/0112885 A1 | 5/2008 | Okunev et al. |
| 2008/0114224 A1 | 5/2008 | Brandy |
| 2008/0129457 A1 | 6/2008 | Ritter et al. |
| 2008/0191581 A9 | 8/2008 | Penner et al. |
| 2008/0288038 A1 | 11/2008 | Paul et al. |
| 2008/0312719 A1* | 12/2008 | Keilman ......................... 607/60 |
| 2009/0074216 A1* | 3/2009 | Bradford et al. .............. 381/315 |
| 2009/0075687 A1 | 3/2009 | Hino et al. |
| 2009/0177251 A1 | 7/2009 | Huelskamp et al. |
| 2010/0042177 A1 | 2/2010 | Stahmann et al. |

FOREIGN PATENT DOCUMENTS

| | | |
|---|---|---|
| JP | 03-034196 | 2/1991 |
| JP | 10-055202 | 2/1998 |
| WO | WO99/34453 | 7/1999 |
| WO | WO99/34731 | 7/1999 |
| WO | WO2004/089465 | 10/2004 |
| WO | WO2006/045073 | 4/2006 |
| WO | WO2006/045074 | 4/2006 |
| WO | WO2006/045075 | 4/2006 |
| WO | WO2006/069215 | 6/2006 |
| WO | 2007070794 | 6/2007 |
| WO | WO2008/011592 | 1/2008 |
| WO | WO2008/011593 | 1/2008 |
| WO | 2009102640 A1 | 8/2009 |

* cited by examiner

DIRECT INDUCTIVE/ACOUSTIC CONVERTER FOR IMPLANTABLE MEDICAL DEVICE

CROSS-REFERENCE TO RELATED APPLICATION

This application claims priority under 35 U.S.C. §119 to U.S. Provisional Application No. 61/026,607, filed on Feb. 6, 2008, entitled "Direct Inductive/Acoustic Converter For Implantable Medical Device," which is incorporated herein by reference in its entirety.

TECHNICAL FIELD

The present disclosure relates generally to medical devices implantable within the body. More specifically, the present disclosure pertains to systems and methods for communicating with and powering implantable medical devices using a direct inductive/acoustic link.

BACKGROUND

Implantable medical devices (IMD's) such as pacemakers and implantable cardioverter defibrillators are frequently utilized in monitoring and regulating various conditions within the body. An implantable cardioverter defibrillator, for example, may be utilized in cardiac rhythm management applications to monitor the rate and rhythm of the heart and for delivering various therapies such as cardiac pacing, cardiac defibrillation, and/or cardiac therapy. In some cases, the implantable medical device can be configured to sense various physiological parameters occurring in the atria and/or ventricles of the body to determine the occurrence of any abnormalities in the operation of the patient's heart. Based on these sensed parameters, the medical device may then deliver an appropriate treatment to the patient.

Communication with implantable medical devices is often accomplished via a telemetry link between an external device and an implanted medical device such as a pulse generator. Typically, telemetric communication between the external device and the pulse generator is accomplished using an inductive or RF link. An example inductive link utilizes an inductive coil which, when energized by an external voltage source, produces an inductive field that can be used to transmit communications signals and/or charging signals to the implanted device. An example RF link, in turn, utilizes dynamic RF (i.e., electromagnetic waves) to transmit communications signals and/or charging signals to the implanted device. In some techniques, telemetric communication between the external programming device and the implanted device can be accomplished using an acoustical link provided by an ultrasonic transducer. Other telemetry methods have also been employed for coupling external devices to implantable medical devices.

Due to their size, conventional IMD's are typically implanted in remote regions within the body away from the source of the signal or the target of the therapy. In some cardiac rhythm management applications, for example, the IMD is implanted in the pectoral or abdominal region of the patient, and includes leads that provide an interconnect between the IMD and the other devices implanted within the body. In some cases, it may be desirable to sense physiological parameters or therapeutic functions at a location within the body having a limited space or volume, requiring the packaging, battery, and associated electronics to be made small to reduce device size.

SUMMARY

The present disclosure pertains to systems and methods for communicating with or powering implantable medical devices using a direct inductive/acoustic link. An exemplary system for communicating with or powering one or more remote devices located within the body of a patient includes an interrogator/programmer device located outside of the patient's body, an implantable medical device including an energy translator circuit adapted to convert inductive or RF signals received from the interrogator device into an acoustic signal for driving an acoustic transducer, and a remote device adapted to sense one or more parameters within the body or to provide electrical therapy to the body. In some embodiments, the electric circuit for the remote implantable medical device includes an inductor coil in series or parallel with an ultrasonic transducer. The inductor coil can be placed into an electrical resonance mode with the ultrasonic transducer via an interrogation signal tuned to the resonance frequency of both the inductor coil and the ultrasonic transducer, or at a resonance frequency of the inductor coil and a harmonic of the ultrasonic transducer. In some embodiments, a switching circuit can be provided for switching the implantable medical device between a communications mode of operation for communicating with the implantable medical device or a charging mode of operation for recharging the remote device.

An exemplary method for communicating with or powering one or more remote devices located within the body includes transmitting an inductive or RF interrogating signal to an implantable medical device located within the body, converting the signal received from the interrogator device into an acoustic signal, and transmitting the acoustic signal to one or more remote devices located within the body. The remote device in one embodiment is configured to sense one or more parameters within the body and then transmit an acoustic data signal back to the implantable medical device or to one or more other medical devices located within the body. The implantable medical device can be configured to convert the acoustic data signal received into a electrical data signal, which can then be transmitted to the interrogator/programmer device and/or another device located outside of the patient's body.

While multiple embodiments are disclosed, still other embodiments of the present invention will become apparent to those skilled in the art from the following detailed description, which shows and describes several illustrative embodiments. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
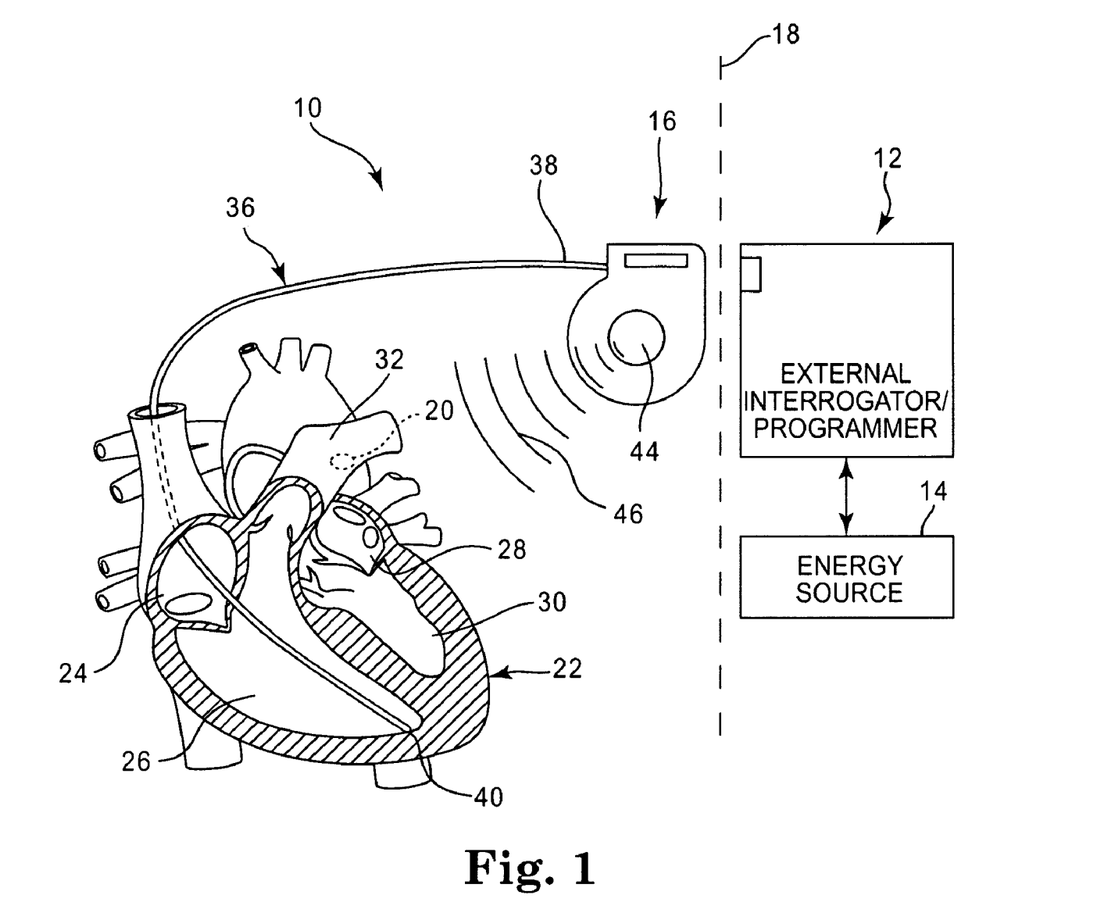
FIG. 1 is a schematic view of an illustrative system for communicating with and/or powering one or more remote sensors located within the body of a patient.

FIG. 1 is a schematic view of an illustrative system 10 for communicating with, powering, and/or recharging one or more remote devices located within the body of a patient. The system 10, illustratively a cardiac rhythm management system for providing cardiac rhythm management to a patient, includes an external interrogator device 12 (e.g., a programmer) coupled to an energy source 14, a pulse generator 16 implanted within the body at a location below the patient's skin 18, and a remote sensing device 20 implanted deeply within the patient's body such as in one of the arteries or ventricles of the patient's heart 22, or at some other desired location within the body. According to other embodiments, the system 10 is any implantable medical device known in the art. The heart 22 includes a right atrium 24, a right ventricle 26, a left atrium 28, and a left ventricle 30. The right ventricle 26 leads to the main pulmonary artery 32 and the branches of the main pulmonary artery. Typically, the pulse generator 16 will be implanted at a location adjacent to the location of the interrogator 12, which may lie adjacent to the exterior surface of the patient's skin 18.

In the illustrative CRM system 10 depicted, the pulse generator 16 is coupled to a lead 36 deployed in the patient's heart 22. As shown, the pulse generator 16 can be implanted subcutaneously within the body, typically at a location such as in the patient's chest or abdomen, although other implantation locations are possible. A proximal portion 38 of the lead 36 can be coupled to or formed integrally with the pulse generator 16. A distal portion 40 of the lead 36, in turn, can be implanted within a desired location within the heart 22 such as the right ventricle 26, as shown. Although the illustrative system 10 depicts only a single lead 36 inserted into the patient's heart 22, it should be understood, however, that the system 10 may include multiple leads so as to electrically stimulate other areas of the heart 22. In some embodiments, for example, the distal portion of a second lead (not shown) may be implanted in the right atrium 24. In addition, or in lieu, another lead may be implanted at the left side of the heart 22 (e.g., in the coronary veins) to stimulate the left side of the heart 22. Other types of leads such as epicardial leads may also be utilized in addition to, or in lieu of, the lead 36 depicted in FIG. 1.

During operation, the lead 36 can be configured to convey electrical signals between the heart 22 and the pulse generator 16. For example, in those embodiments where the pulse generator 16 is a pacemaker, the lead 36 can be utilized to deliver electrical therapeutic stimulus for pacing the heart 22. In those embodiments where the pulse generator 16 is an implantable cardiac defibrillator, the lead 36 can be utilized to deliver electric shocks to the heart 22 in response to an event such as a heart attack. In some embodiments, the pulse generator 16 includes both pacing and defibrillation capabilities.

The remote device 20 can be configured to perform one or more designated functions, including the sensing of one or more physiological parameters within the body. Example physiological parameters that can be measured using the remote device 20 can include, but are not limited to, blood pressure, blood flow, temperature, and strain. Various electrical, chemical and/or magnetic properties may also be sensed within the body via the remote device 20. The specific configuration and location of the remote device 20 will typically vary depending on the particular therapeutic needs of the patient. In one illustrative embodiment, for example, the remote device 20 includes a pressure sensor that can be implanted at a desired location deep within the body such as the main pulmonary artery 32 or a branch of the main pulmonary artery 32 (e.g., in the right or left pulmonary artery). An illustrative pressure sensor that can be used in some embodiments is described in U.S. Pat. No. 6,764,446, entitled "Implantable Pressure Sensors and Methods for Making and Using Them," the contents of which are incorporated herein by reference in their entirety. In use, the pressure sensor can be used to predict decompensation of a heart failure patient or to optimize pacing and/or defibrillation therapy. It should be understood, however, that the remote device 20 can be implanted at other locations within the body, and can be configured to measure other parameters. Moreover, although a single remote device 20 is depicted in FIG. 1, multiple such devices can be implanted at various locations within the body for sensing physiologic parameters at multiple regions within the body.

The remote device 20 can be tasked, either alone or with other implantable devices, to provide various therapies within the body. In certain embodiments, for example, the remote device 20 may comprise a glucose level sensor which can be used in conjunction with an insulin pump for providing insulin to the patient. In other embodiments, the remote device 20 can comprise a pulmonary sound sensor, a satellite pacing device, or other such sensing and/or therapy-delivering device.

Figure 2:
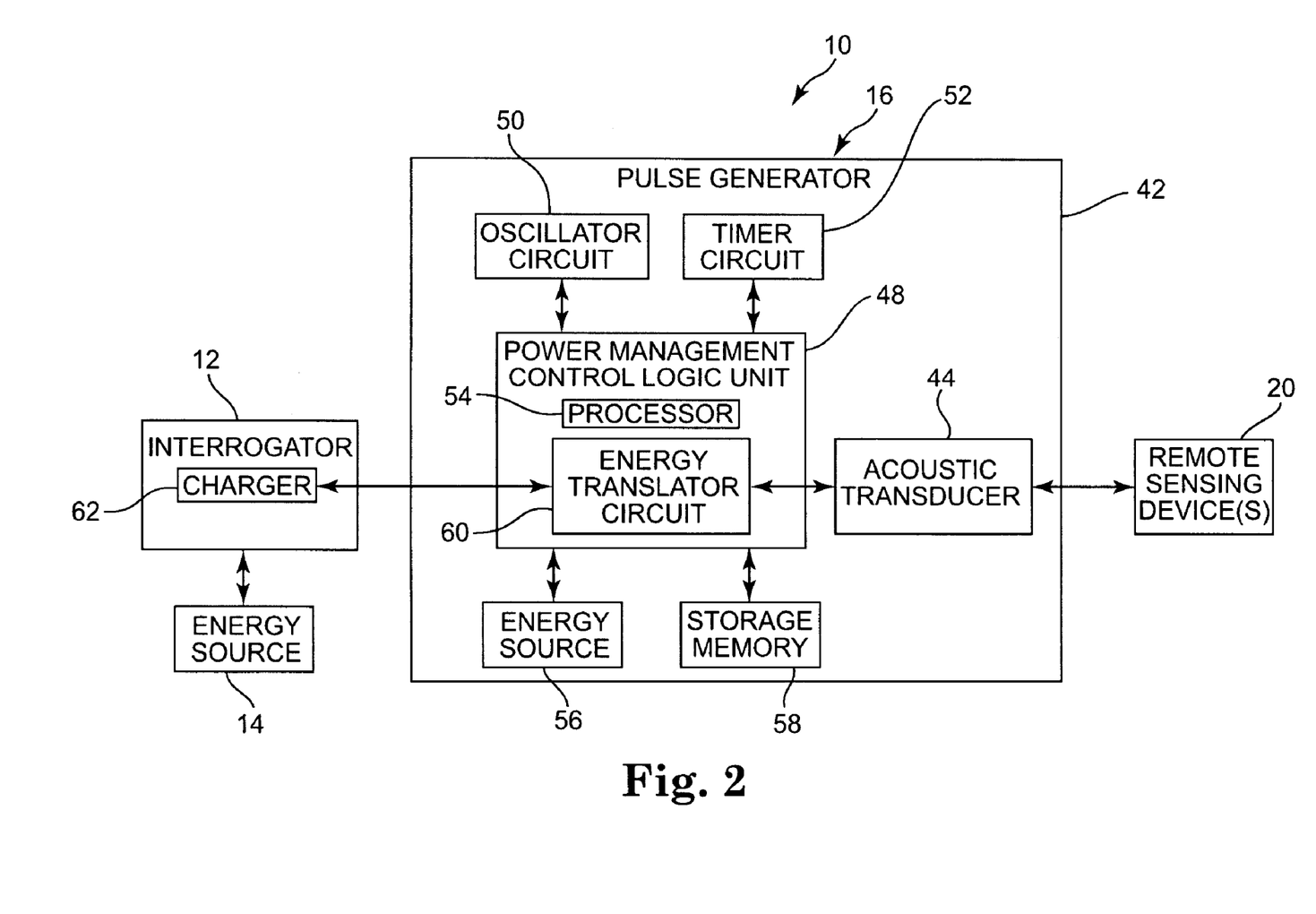
FIG. 2 is a block diagram showing several illustrative components of the system of FIG. 1.

FIG. 2 is a block diagram showing several illustrative components of the system 10 of FIG. 1. As shown in FIG. 2, the pulse generator 16 can include a housing or can 42, which functions as a hermetically sealed enclosure for the pulse generator circuitry and components. In some cases, for example, the can 42 includes a casing formed from titanium or the like, and includes one or more regions that facilitate the passage of acoustic energy through the can 42. The pulse generator 16 includes an ultrasonic transducer 44, which as is shown in FIG. 1, is configured to generate and receive acoustic waves 46 for communicating with and/or powering the remote device 20 via an acoustic telemetry link. Although a single ultrasonic transducer 44 can be configured to both transmit and receive acoustic signals within the body, in alternative embodiments multiple transducers are implemented. In some embodiments, for example, separate ultrasonic transducers are utilized for transmitting and receiving acoustic waves.

The ultrasonic transducer 44 can be incorporated into the housing or can 42 for the pulse generator 16. In some embodiments, for example, the ultrasonic transducer 44 is coupled to an inner surface of the can 42, or is coupled to a header on the can 42. Alternatively, and in other embodiments, the ultrasonic transducer 44 is provided through a feed-through connection on the pulse generator 16. In other embodiments, the ultrasonic transducer 44 is coupled to the can 42 using any other technique known in the art.

In certain embodiments, the ultrasonic transducer 44 includes a resonant structure such as a flexible diaphragm or element that can be coupled to the can 42 in a manner to facilitate the transmission of acoustic waves. In some embodiments, for example, the ultrasonic transducer 44 comprises a number of flexible piezoelectric elements adapted to resonate at a particular frequency in response to excitation from the interrogator 12. An example of an acoustic transducer suitable for use in the present system 10 is described in U.S. patent application Ser. No. 12/122,431, entitled "Acoustic Transducer For An Implantable Medical Device," the contents of which are incorporated herein by reference in their entirety. In other embodiments, however, the specific configuration of the transducer may be different from that described therein.

A power management and control logic unit 48 for the pulse generator 16 provides control circuitry for the pulse generator 16, including an electrical circuit that can be used to establish a direct inductive/acoustic telemetry link between the interrogator 12 and the remote device 20, as discussed further herein. The unit 48 can be coupled to other components of the pulse generator 16, including an oscillator circuit 50 for driving the ultrasonic transducer 44, and a timer circuit 52 for taking time and date measurements. In some embodiments, the unit 48 further includes a processor 54 for processing data received from the ultrasonic transducer 44 as well as information from any other devices and/or components coupled to the pulse generator 16.

The pulse generator 16 can further include an energy source 56 such as a rechargeable battery or power capacitor, allowing at least a portion of the pulse generator 16 to remain active at all times. A storage memory 58 (e.g., flash memory or ferroelectric memory) coupled to the energy source 56 is used to provide storage of data received from the remote device 20, commands used for controlling the pulse generator 16 and remote device 20, usage data, as well as other information. The storage memory 58 may be a temporary buffer that holds data before transfer to another device, or a non-volatile memory capable of storing the data for a substantially indefinite period of time. In some embodiments, for example, the storage memory 58 is configured to store a unique identification code for the pulse generator 16 that can be used to uniquely identify the pulse generator 16 from other components within the system 10.

In some embodiments, and as further shown in FIG. 2, the electrical circuit for the pulse generator 16 includes an energy translator circuit 60 for providing a direct inductive/acoustic telemetry link between the interrogator device 12 and the remote device 20. As detailed below, in some embodiments the energy translator circuit 60 is configured to convert the inductive signals received from the interrogator device 12 into acoustic signals that can be transmitted by the ultrasonic transducer 44 to the remote device 20 for charging the device 20 and/or for communicating with the device 10. In certain embodiments, for example, the interrogator device 10 includes an external charger 62 (e.g., an external inductor coil) that can be paired with a corresponding inductor coil within the pulse generator 16. The external charger 62 can be coupled to an electrical energy source 14 such as an RF generator to produce an inductive field within the paired inductor coils. This induced inductive field can then be utilized to drive the ultrasonic transducer 44 into an electrical resonance mode, either at its primary resonance frequency or at a harmonic of this frequency. In some embodiments, this induced resonance within the translator circuit 60 can also be utilized to passively power the pulse generator 16, reducing the power load demanded on the energy source 56.

Figure 3:
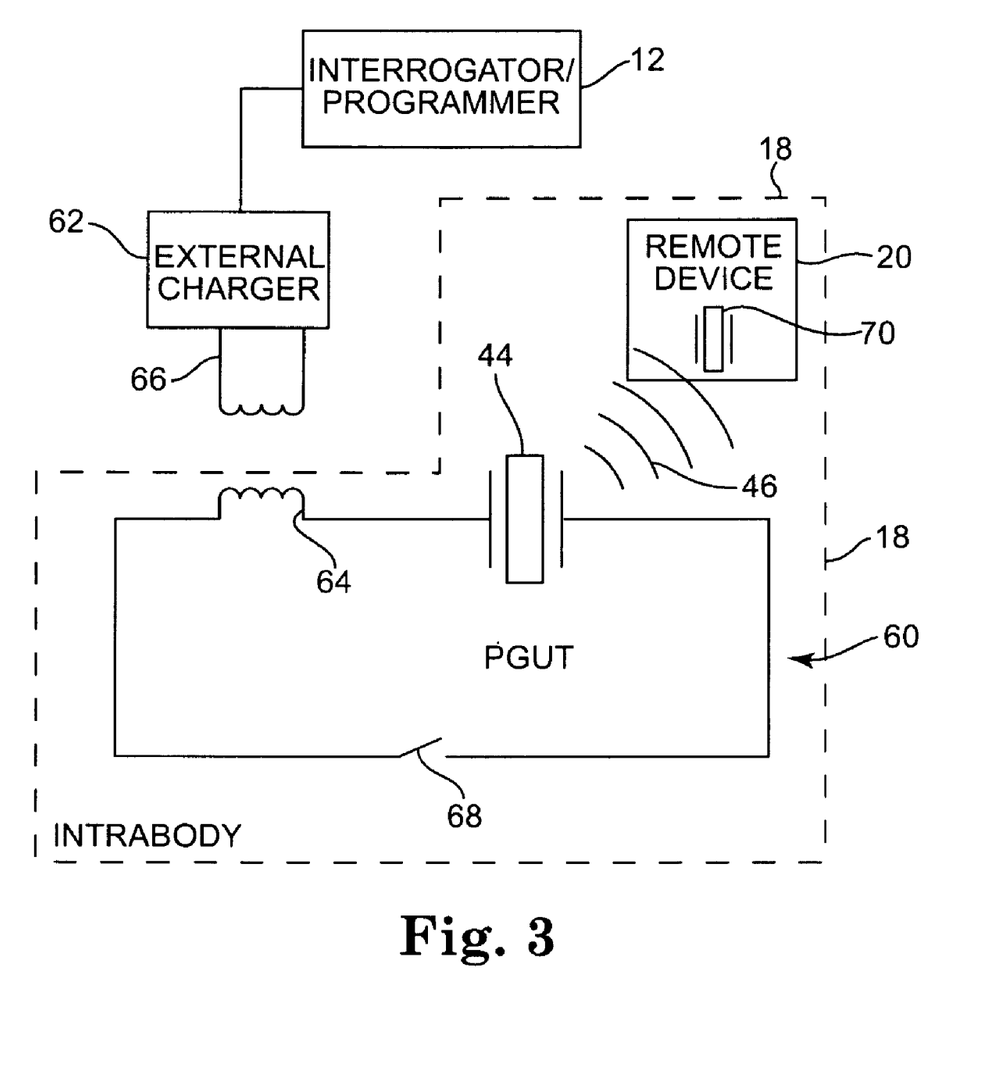
FIG. 3 is a schematic diagram showing a direct inductive/acoustic energy translator circuit in accordance with an illustrative embodiment.

FIG. 3 is a schematic diagram showing a series-tuned direct inductive-acoustic energy translator circuit 60 in accordance with an illustrative embodiment. In the illustrative embodiment of FIG. 3, the translator circuit 60 comprises a single LC circuit loop formed by an inductor coil 64 inductively coupled to an externally powered coil 66, and the ultrasonic transducer 44, which for a piezoelectric ultrasonic transducer, functions within the circuit 60 as a capacitor in series with the inductor coil 64. Although the illustrative embodiment of FIG. 3 depicts a series-tuned translator circuit 60, a parallel-tuned translator circuit can also be used.

The inductance of the inductor coil 64 and the capacitance of the ultrasonic transducer 44 can be configured so as to induce a resonance mode within the translator circuit 60, allowing the inductive signal from the interrogator device 12 to directly control the charging and/or communication of the remote device 20, thereby reducing the complexity of the pulse generator electronics. For many intrabody applications, inductive telemetry is effective in the range of about 20 KHz to about 200 KHz. To increase the effectiveness of the inductive link, therefore, the values of the inductance and capacitance of the LC loop should be chosen so as to induce resonance within this frequency range. Assuming, for example, that the ultrasonic transducer 44 has a capacitance of about 10 nF, an acceptable inductance for the inductor coil 64 to induce resonance in the LC loop is about 88 µH. The particular values may differ, however, depending on the mechanical characteristics of the ultrasonic transducer 44, the frequency of the voltage signal applied to the external coil 66, the electrical characteristics of the inductor coil 64, as well as other factors.

In some embodiments, a switch 68 in series within the inductor coil 64 and the ultrasonic transducer 44 is selectively switched on or off to operate the pulse generator 16 in one of either a communications mode of operation or a recharging mode of operation. In a communications mode of operation, for example, the switch 68 can be opened to switch-out the ultrasonic transducer 44 from the translator circuit 60. When this occurs, the inductor coil 44 can be utilized to establish an inductive telemetric link for communications between the interrogator device 12 and the pulse generator 16 without operation of the ultrasonic transducer 44. Conversely, in a charging mode of operation, the switch 68 can be closed to switch-in the ultrasonic transducer 44 into the translator circuit 60. In this mode, the ultrasonic transducer 44 transmits an acoustic signal 46 that is received by an ultrasonic transducer 70 operatively coupled to the remote device 20. The acoustic signal 46 transmitted by the ultrasonic transducer 44 can be utilized, for example, for passively powering and/or charging the remote device 20, or to provide communications back and forth between the remote device 20 and the pulse generator 16.

The ultrasonic transducer 44 for the pulse generator 16 can be configured to resonate at a frequency at or near the frequency of the inductive link to permit the ultrasonic transducer 44 to operate with greater efficiency when activated. In certain embodiments, for example, the ultrasonic transducer 44 can be configured to resonate at a frequency at or about 120 KHz, similar to the interrogation frequency used to establish the inductive link. Because the sensitivity of the ultrasonic transducer 44 is typically greatest at its resonance frequency, the power required to drive the transducer 44 and produce the acoustic signal 46 is typically lower, resulting in less power demand on the pulse generator 16 and/or the external interrogator 12.

In some embodiments, the interrogation frequency can be selected to correspond to a particular harmonic of the resonance frequency of the ultrasonic transducer 44. For certain ultrasonic transducers having a resonance frequency at or near about 40 KHz, for example, the interrogation frequency of the interrogator signal (e.g., 120 KHz) may correspond to a harmonic of the resonance frequency for the ultrasonic transducer 44. Because the sensitivity of the ultrasonic transducer 44 increases significantly at each harmonic, the interrogation signal can be utilized for both providing the inductive link between the interrogator device 12 and the pulse generator 16 as well as the acoustic link between the pulse generator 16 and the remote device 20.

In some embodiments, the translator circuit 60 further includes a tuner for tuning the resonance characteristics of the inductor coil 64 and/or the ultrasonic transducer 44. In one alternative embodiment depicted in FIG. 4, for example, the translator circuit 60 includes a tuning inductor 72 that can be selectively introduced into the circuit 60 via a switch 74 to alter the inductance within the circuit 60. When switched into the circuit 60, the tuning inductor 72 can be configured to adjust the resonance frequency in order to tune the circuit 60 to function in a certain manner based on the particular mode of operation. In certain embodiments, for example, the inductor 72 can be switched into the translator circuit 60 when the ultrasonic transducer 44 is activated during the charging mode of operation in order to increase the sensitivity of the transducer 44. Alternatively, the inductor 72 can be switched out of the translator circuit 60 during the communications mode of operation in order to increase the coupling coefficient of the paired inductor coils 64,66 for greater efficiency in the inductive link.

Figure 5:
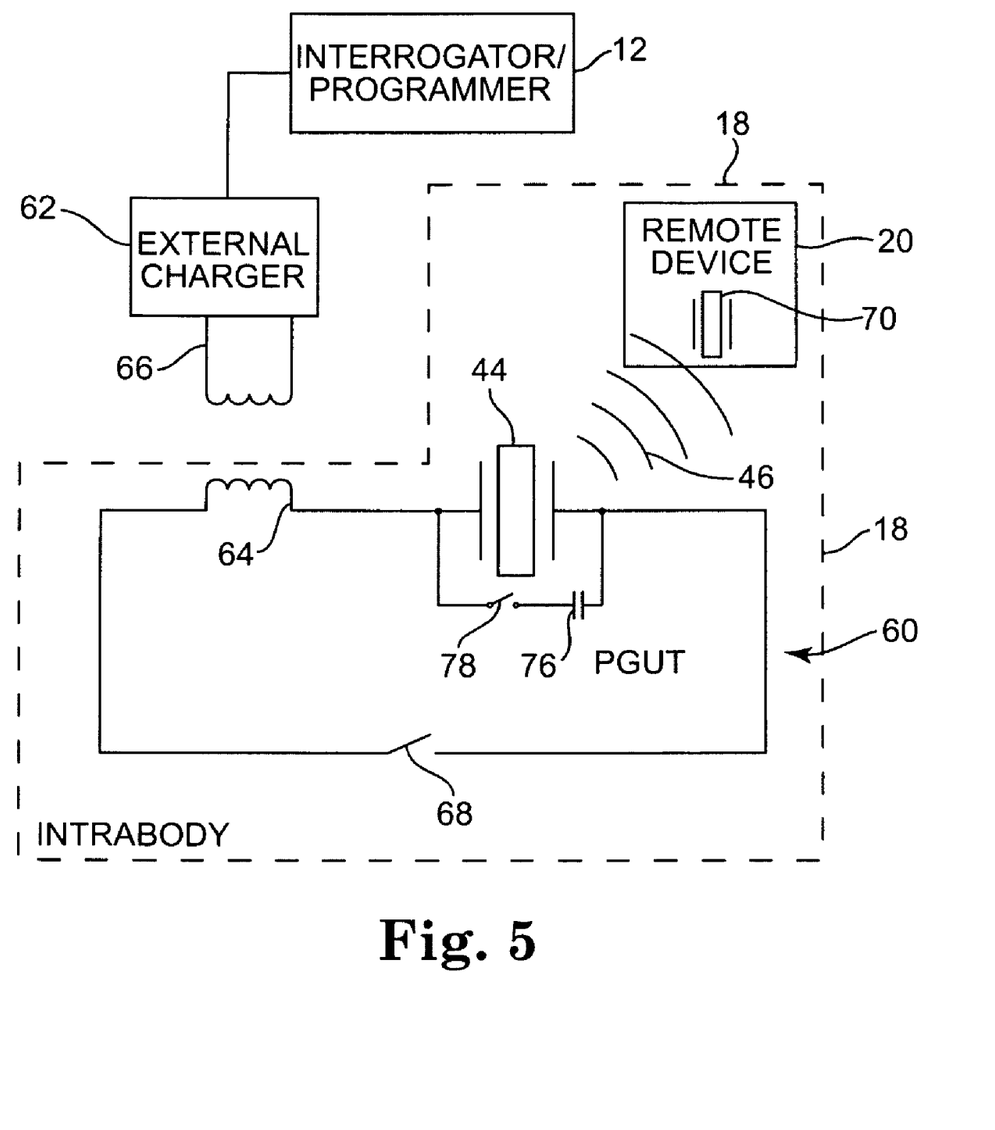
FIG. 5 is a schematic diagram showing a direct inductive/acoustic energy translator circuit in accordance with another illustrative embodiment having a capacitive tuner.

In another alternative embodiment depicted in FIG. 5, the translator circuit 60 further includes a tuning capacitor 76 (e.g., a programmable capacitor) that can be selectively introduced into the circuit 60 to alter the capacitance within the circuit 60. The introduction of the capacitor 76 can be configured to further tune the translator circuit 60 to operate at a particular resonance frequency based on the desired mode of operation. In some embodiments, for example, the capacitor 76 is switched into the circuit 60 at times when greater sensitivity in the ultrasonic transducer 44 is required, such as during the transmission and/or reception of data signals back and forth between the remote device 20 and the pulse generator 16.

Figure 4:
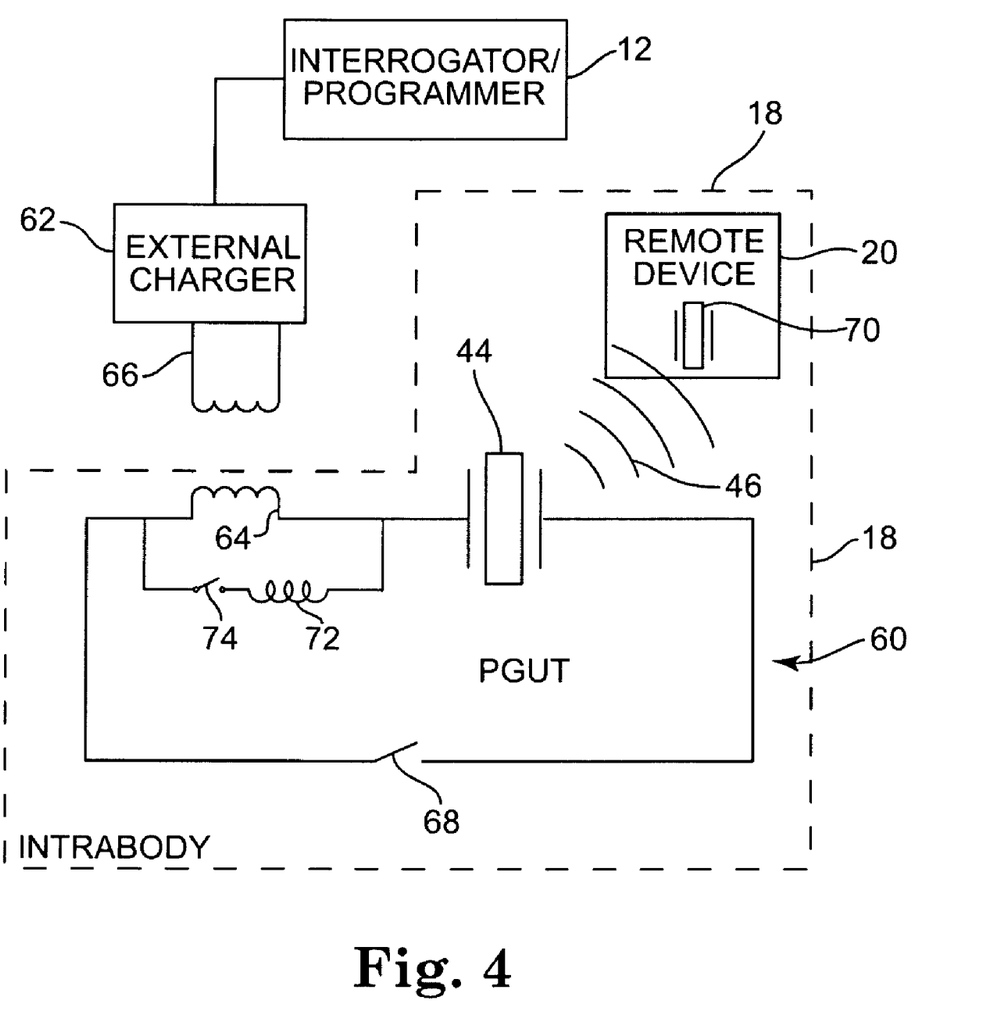
FIG. 4 is a schematic diagram showing a direct inductive/acoustic energy translator circuit in accordance with another illustrative embodiment having an inductive tuner.

The regulation of the tuning inductor 72 and/or tuning capacitor 76 can be accomplished via a controller within the pulse generator 16 or, alternatively, via control signals received from the interrogator device 12. In some embodiments, the tuning inductor 72 and/or tuning capacitor 76 is fabricated on the same IC chip as the other components of the translator circuit 60, including the inductive coil 64, ultrasonic transducer 44, and the switch 68.

Although the embodiments depicted in FIGS. 4 and 5 utilize a separate tuner (e.g., a tuning inductor or tuning capacitor) for tuning either the inductive or capacitive reactance, other embodiments employ multiple inductive and/or capacitive tuners. In one alternative embodiment, for example, both a tuning inductor coil and capacitor are simultaneously switched into the translator circuit 60 for tuning the resonance characteristics of the circuit 60. Other means for tuning the translator circuit are also possible.

In some embodiments, the ultrasonic transducer 44 itself may serve as a capacitive tuner for the inductive coil 64. In certain embodiments, for example, the ultrasonic transducer 44 includes a number of damper electrodes (not shown) that can be utilized to either increase or decrease the damping of the piezoelectric element of the transducer 44 in order to adjust the resonance frequency of the element. Other means for selectively adjusting the frequency characteristics of the ultrasonic transducer 44 can also be employed.

The frequency of the interrogation voltage signal provided by the external charger 62 can be varied depending on whether the pulse generator 16 is operating in the communications mode or the charging mode. In a communications mode, for example, the interrogation voltage signal may have a frequency that is relatively high whereas, in the charging mode when the ultrasonic transducer 44 is activated, the interrogation voltage signal may be relatively low. By way of example and not limitation, the frequency of the interrogation voltage signal in the communications mode may be about 120 kHz, which as discussed above, is a frequency useful for inductive telemetry communications through the body. The frequency of the interrogation voltage signal in the charging mode, in turn, may be at or near the resonant frequency of the ultrasonic transducer 44, or alternatively, one of its harmonics. In some embodiments, for example, the frequency of the interrogation voltage signal in the charging mode may be about 40 kHz.

Figure 6:
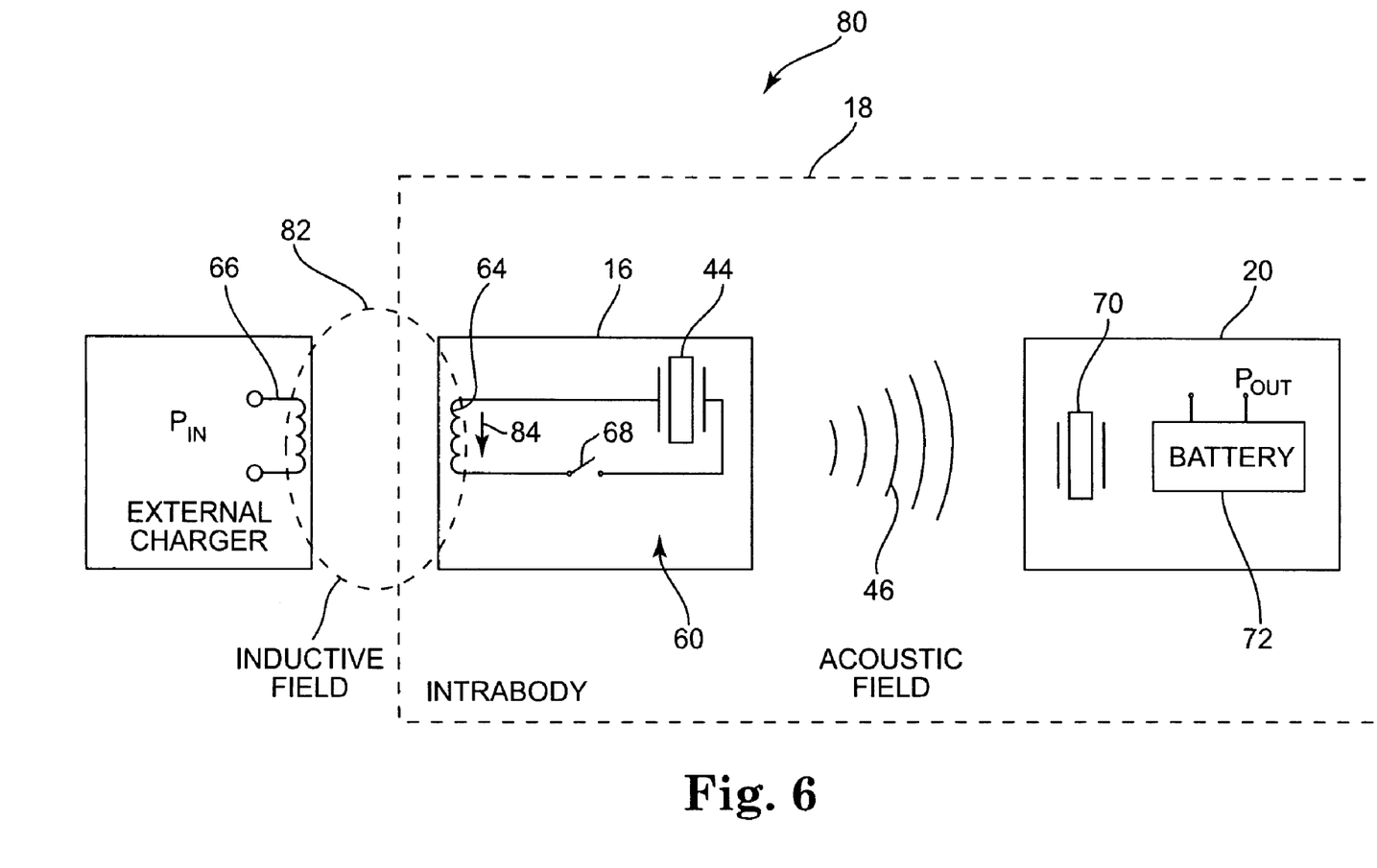
FIG. 6 is a schematic diagram showing an illustrative method of communicating with and/or powering a remote device using the energy translator circuit of FIG. 3.

FIG. 6 is a schematic diagram showing an illustrative system 80 of establishing a direct inductive/acoustic link using the energy translator circuit 60 of FIG. 3. As shown in FIG. 6, an interrogation voltage PIN applied to the external charger 62 can be configured to produce an inductive field 82 at the body interface 18 due to the magnetic coupling between the internal and exterior inductor coils 64,66. The resultant inductive field 82 produces an electrical signal 84 within the internal inductive coil 64, which, in turn, is fed to the ultrasonic transducer 44 when activated by the switch 68. If desired, the electrical signal 84 produced can be used for performing other functions such as powering the pulse generator 16 or for recharging the battery of the pulse generator 16.

Figure 7:
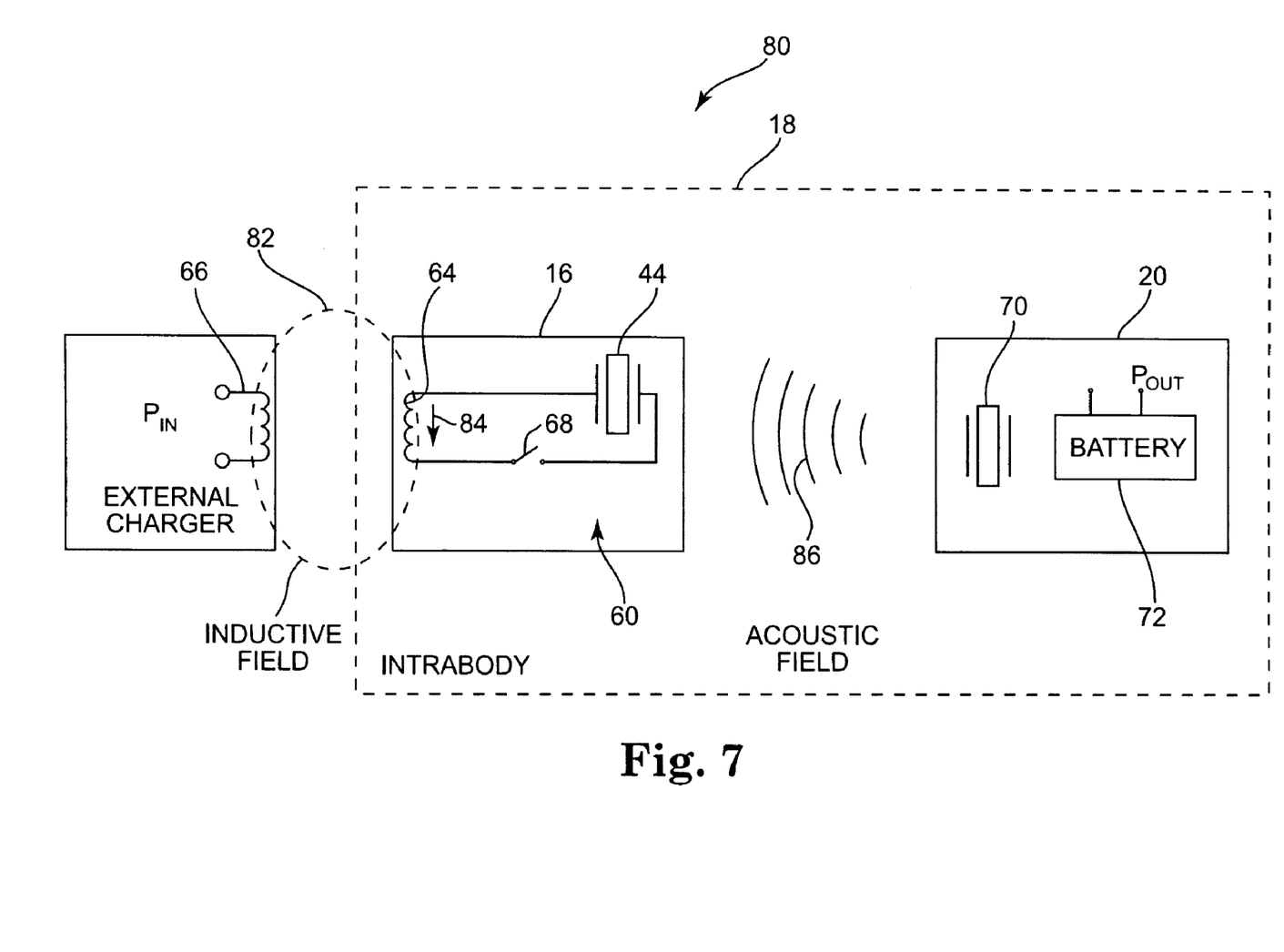
FIG. 7 is another schematic diagram of the system of FIG. 6 showing the transmission of an acoustic field from the remote device to the pulse generator.

When activated, and as further shown in FIG. 6, the ultrasonic transducer 44 can be configured to produce an acoustic field 46 within the body, which can be received by the ultrasonic transducer 70 for the remote device 20. The transducer 70 and charging control circuit can then convert the acoustic energy received into an output voltage POUT that can be used for recharging a rechargeable power source such as a battery 72 operatively coupled to the device 20. As can be further seen in FIG. 7, the remote device 20 may transmit an acoustic field 86 back to the pulse generator 16 that includes sensor readings taken by the device 20, diagnostics information (e.g., power status information, operational information), as well as other information.

Figure 8:
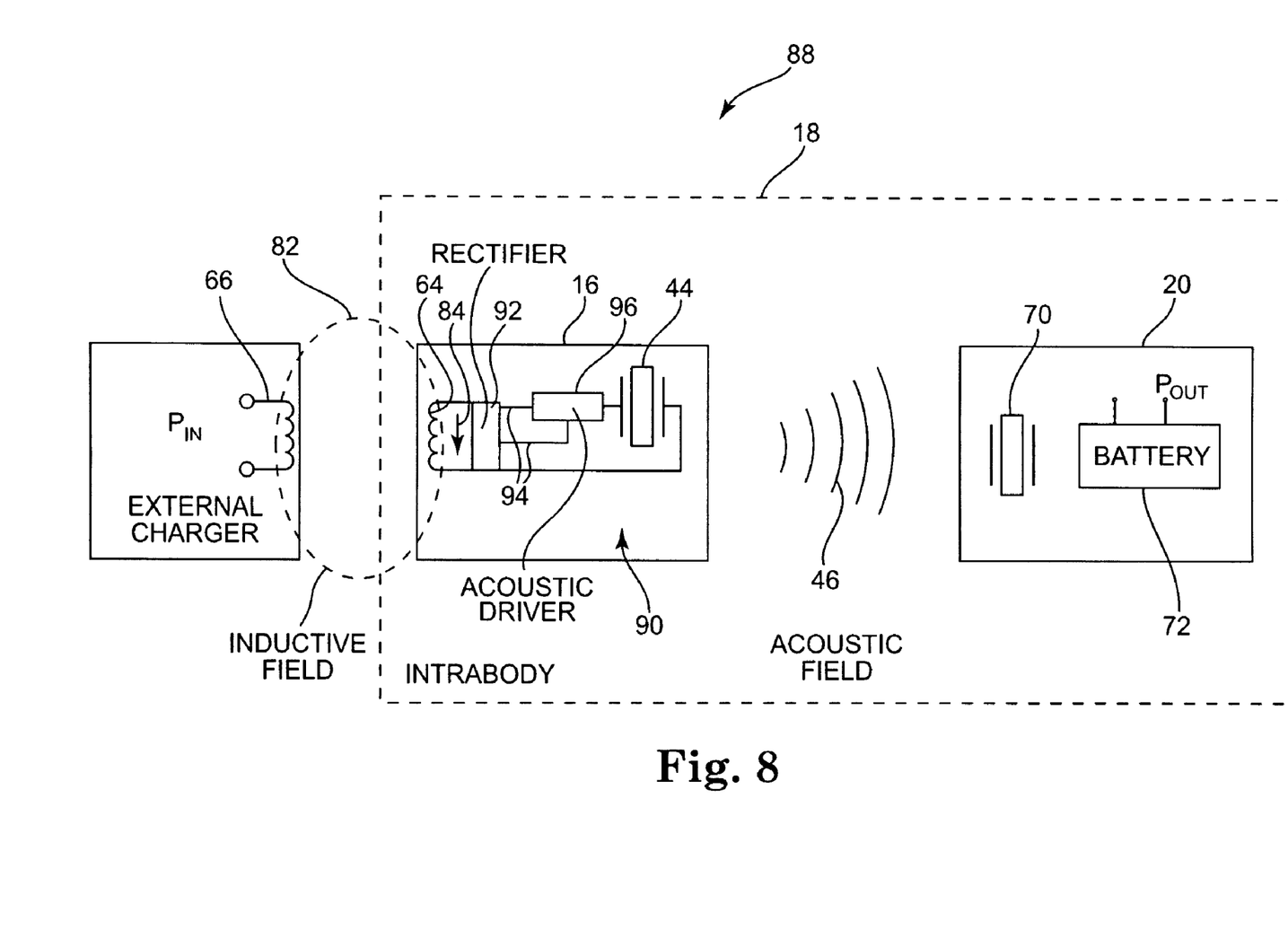
FIG. 8 is a schematic diagram showing a direct inductive/acoustic energy translator circuit in accordance with another illustrative embodiment employing a rectifier circuit.

In some embodiments, the translator circuit 60 further includes a rectifier circuit to convert the inductive or RF signals into DC signals, which can then be converted to an acoustic signal for transmission to the remote device 10. In one embodiment system 88 shown in FIG. 8, for example, the translator circuit 90 includes a rectifier circuit 92 that converts the time-varying inductive or RF signals into DC signals 94. In some embodiments, for example, the rectifier circuit 92 comprises a full wave rectifier circuit which converts the time-varying signals received by the inductor coil 64 into corresponding DC signals 94. An acoustic driver 96 coupled to the rectifier circuit 92 is configured to drive the ultrasonic transducer 44 based on the DC signals 94 outputted by the rectifier circuit 92.

Because an inductive link is provided for communicating through the patient's skin 18 and into the body, charging of the remote device 20 and/or pulse generator 16 can be accomplished without the use of a gel or other such interface coupling material commonly used in acoustic systems for impedance matching. Moreover, because an acoustic telemetry link is provided for intrabody communications between the pulse generator 16 and the remote device 20, the attenuation losses typically associated with the use of inductive or RF telemetry techniques within the body are also reduced.

Figure 9:
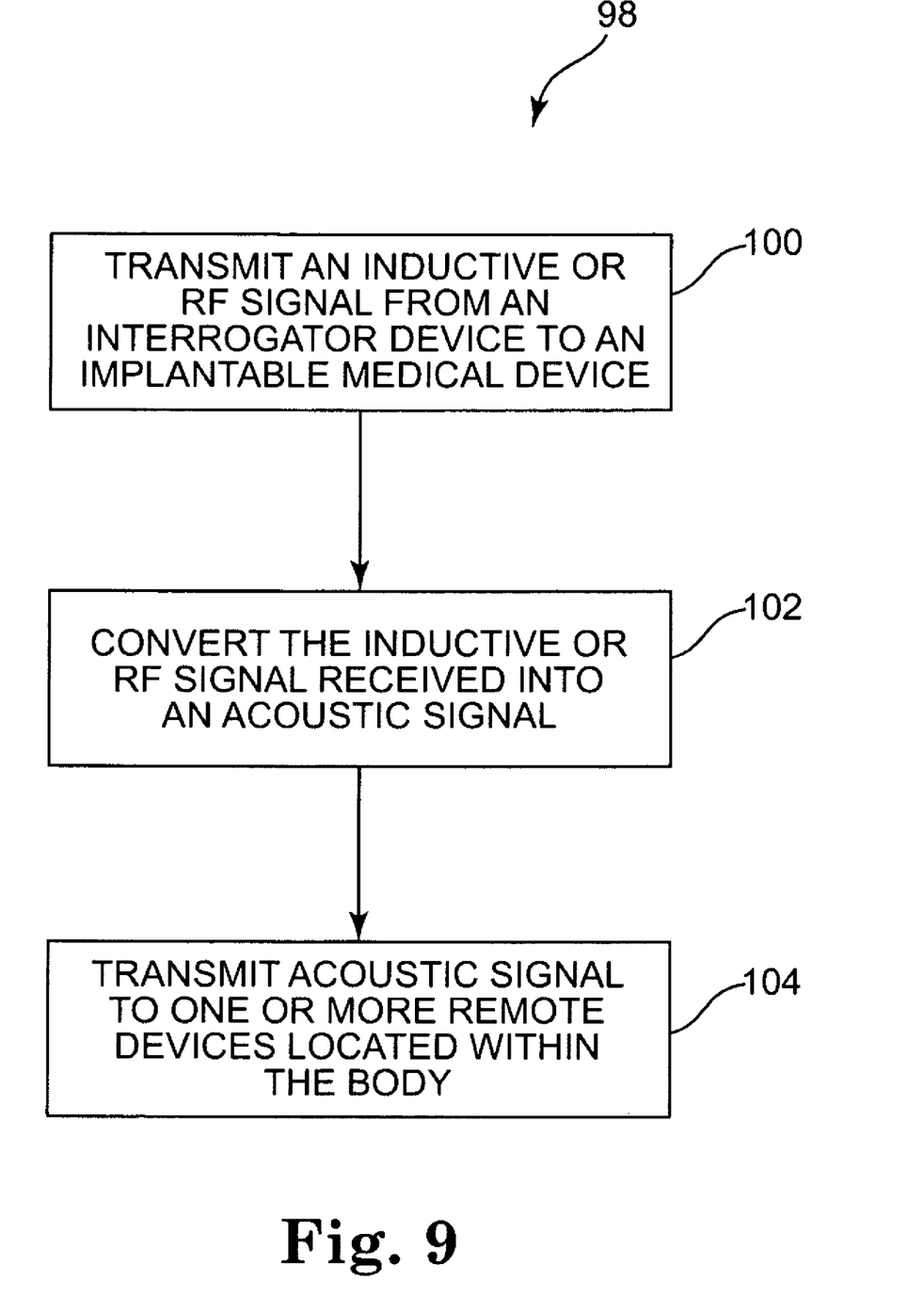
FIG. 9 is a block diagram showing an illustrative method for communicating with and/or powering one or more remote devices located within the body of a patient.

FIG. 9 is a block diagram showing an illustrative method 98 for communicating with and/or powering one or more remote devices located within the body of a patient. The method 98 may begin generally at block 100 with the step of transmitting an inductive or RF signal from an interrogator device to an implantable medical device located within the body. In cardiac rhythm management applications, for example, the interrogator device may comprise a programmer device in communication with an implantable medical device such as a pacemaker or implantable cardiac defibrillator. In other applications such as insulin therapy, the interrogator device may comprise a glucose monitor in communication with an implantable medical device such as an insulin pump. Other configurations, however, are possible.

In some embodiments, and as further illustrated generally at block 102, the inductive or RF signals received from the interrogator device are converted into acoustic signals that can be used to drive the ultrasonic transducer for the implantable medical device. In certain embodiments, for example, the conversion of the inductive or RF signals into acoustic signals can be accomplished using the acoustic energy translator circuit 60 described above with respect to FIG. 3. Once converted, the ultrasonic transducer for the implantable medical device then transmits an acoustic signal to one or more remote devices in communication with the implantable medical device, as indicated generally at block 104.

Figure 10:
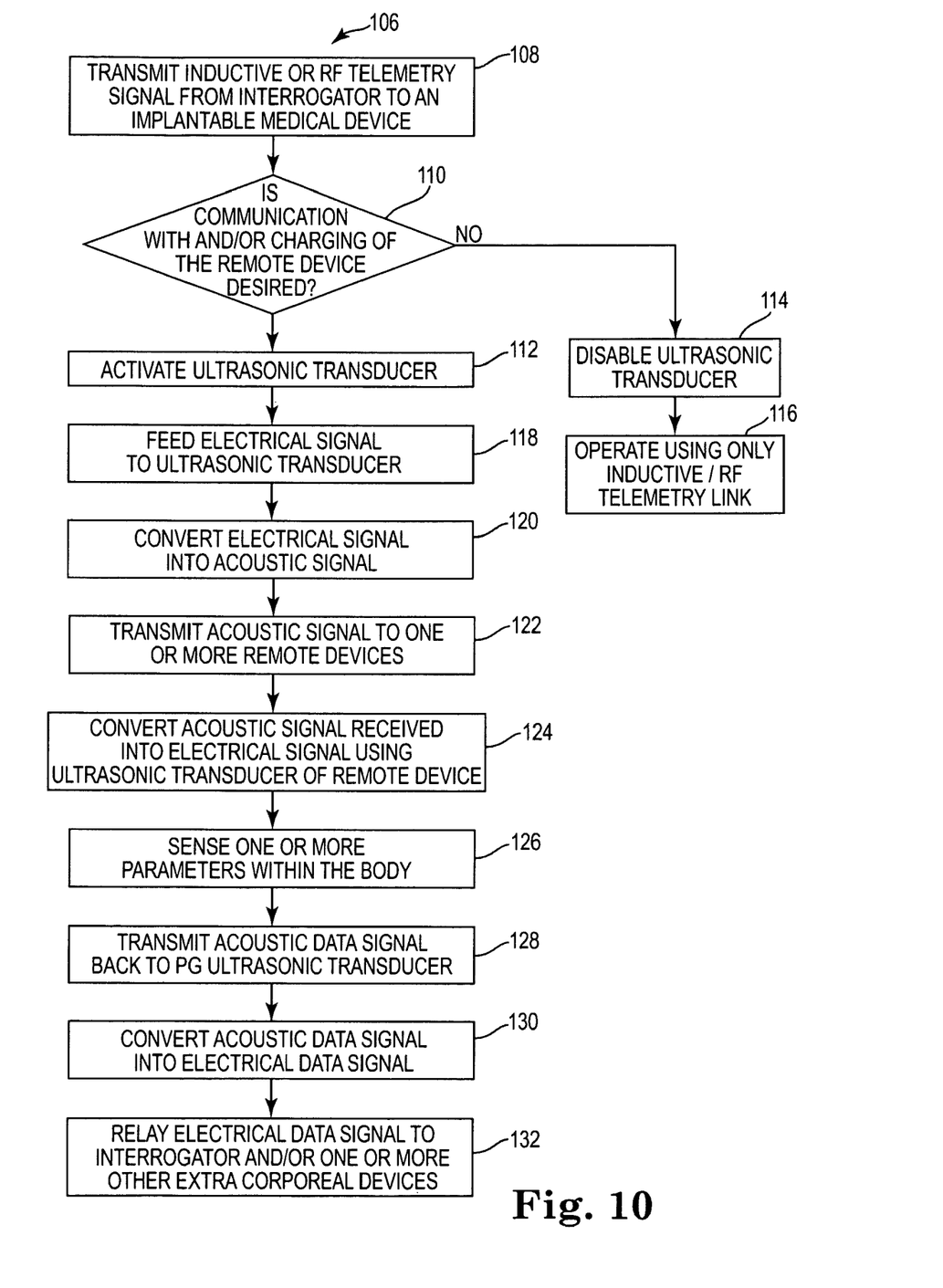
FIG. 10 is a block diagram showing another illustrative method for communicating with and/or powering one or more remote devices located within the body of a patient.

FIG. 10 is a block diagram showing another illustrative method 106 of communicating with and/or powering a remote device located within the body of a patient. The method 106 may begin generally at block 108 with the step of transmitting an inductive or RF signal from an interrogator device to an implantable medical device located within the body. The controller for the pulse generator can be configured to switch between a communications mode of operation to enable communications between the interrogator device and implantable medical device, and a charging mode of operation to enable communications and/or charging of one or more remote devices in acoustic communication with the implantable medical device. If at decision block 110 the pulse generator determines that communications and/or charging of the remote device is desired, the controller for the pulse generator activates the ultrasonic transducer, as indicated generally at block 112. With respect to the illustrative translator circuit 60 of FIG. 3, for example, activation of the ultrasonic transducer 44 can occur by closing the switch 68 via a command signal received by the interrogator/programmer device 12 or from the remote device 20. Alternatively, if communication between only the pulse generator and interrogator device is desired, the controller for the pulse generator can be configured to disable the ultrasonic transducer to temporarily suspend acoustic communications with the remote device, as indicated generally at block 114. When suspended, the pulse generator may operate with only the inductive telemetry link between the pulse generator and the interrogator device, as indicated generally at block 116.

In certain embodiments, whether to activate the ultrasonic transducer is determined by a data signal provided as part of the inductive or RF signal transmitted to the pulse generator from the interrogator device, a signal received from the remote device, or a signal received from some other device located inside or outside of the patient's body. Activation of the ultrasonic transducer can also be accomplished by a controller of the pulse generator, which may activate the transducer at predetermined time periods and/or upon the detection of a physiological event (e.g., ischemia) within the body.

If at block 112 the ultrasonic transducer is activated, the inductive signal received by the pulse generator can be fed as an electrical signal to the ultrasonic transducer, as indicated generally at block 118. The ultrasonic transducer then converts the electrical signals into acoustic signals (block 120), which can then be transmitted to one or more remote devices in acoustic communication with the pulse generator (block 122). Conversion of the inductive signal into an acoustic signal can be accomplished, for example, via the direct inductive/acoustic energy translator circuit 60 described above with respect to FIG. 3.

As further indicated at block 124, the acoustic signals transmitted from the pulse generator to the remote device can then be converted into electrical signals that can be used for powering and/or recharging the remote device as well as to communicate with the remote device. In some embodiments, and as illustrated generally at blocks 126 and 128, the remote device senses one or more parameters within the body, and then transmits an acoustic data signal back to the ultrasonic transducer for the pulse generator. As illustrated further by block 130, the acoustic data signal is then converted into an electrical data signal for use by the pulse generator for providing therapy to the patient. In addition, or in lieu, the electrical data signal can be relayed via the inductive or RF telemetry link to the interrogator device and/or one or more other devices located outside of the patient's body, as indicated generally at block 132.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A system for communicating with or powering one or more remote devices located within the body of a patient, the system comprising:

an interrogator device located outside of the patient's body, the interrogator device including an energy source and an inductor for transmitting an inductive or RF signal into the patient's body;

an implantable medical device including an energy translator circuit, the energy translator circuit comprising an LC resonance loop formed by the inductance of an inductor in wireless communication with the inductor of the interrogator device and the capacitance of an ultrasonic transducer, wherein the LC resonance loop has an electrical resonance mode adapted to convert the inductive or RF signal received from the interrogator device into an acoustic signal for driving the ultrasonic transducer at or near a resonance frequency or natural harmonic frequency of the transducer; and one or more remote devices adapted to sense a physiologic parameter within the body, at least one of the remote devices including an acoustic transducer adapted to receive an acoustic field transmitted by the implantable medical device.

2. The system of claim 1, wherein the inductor includes an inductor coil in series or parallel with the ultrasonic transducer.

3. The system of claim 1, wherein the remote device is further configured to transmit an acoustic field to the implantable medical device.

4. The system of claim 1, wherein the energy translator circuit comprises a single LC loop.

5. The system of claim 1, further comprising a tuner for tuning a capacitance and/or inductance of the energy translator circuit.

6. The system of claim 1, further comprising a tuner for tuning the resonance of the energy translator circuit.

7. The system of claim 1, wherein the implantable medical device is configured to operate in at least one of a communications mode or a charging mode.

8. The system of claim 7, further comprising a switching circuit for switching the implantable medical device between the communications mode and the charging mode.

9. The system of claim 7, wherein the frequency of the inductive or RF signal is different in the communications mode than in the charging mode.

10. The system of claim 1, wherein the frequency of the electrical resonance mode is between about 10 KHz to 200 KHz.

11. The system of claim 1, wherein the interrogator device is a programmer device externally attachable to the patient's body.

12. The system of claim 1, wherein the interrogator device is a charger externally attachable to the patient's body.

13. The system of claim 1, wherein at least one of the remote devices is a pressure sensor module implantable within the heart or in a blood vessel.

14. A method for communicating with or powering one or more remote devices located within the body of a patient, the method comprising:

transmitting an inductive or RF signal from an inductor of an interrogator device to an implantable medical device located within the body, the implantable medical device including an energy translator circuit comprising an LC resonance loop having an electrical resonance mode, wherein the LC resonance loop is formed by the inductance of an inductor in wireless communication with the inductor of the interrogation device and the capacitance of an ultrasonic transducer;

converting, via the energy translator circuit, the inductive or RF signal received from the interrogator device into an acoustic signal for driving the ultrasonic transducer at or near a resonance frequency or natural harmonic frequency of the transducer; and transmitting an acoustic field to one or more remote devices located within the body for communicating with, powering, and/or recharging the remote devices.

15. The method of claim 14, wherein the energy translator circuit is configured for directly converting the inductive or RF signal into an electrical signal for driving the acoustic transducer.

16. The method of claim 15, wherein the inductor includes an inductor coil in series or parallel with the ultrasonic transducer.

17. The method of claim 14, further including:

sensing one or more parameters within the body;

transmitting an acoustic data signal from at least one remote device to the implantable medical device;

converting the acoustic data signal to an inductive data signal; and transmitting the inductive data signal to the interrogator device.

18. A medical device implantable within the body of a patient, comprising:

an energy translator circuit configured to convert inductive or RF signals received from one or more devices located outside of the patient's body into an electrical signal, the energy translator circuit comprising an LC resonance loop formed by the inductance of an inductor coil and the capacitance of an ultrasound transducer in series or parallel with the inductor coil;

wherein the inductor coil is magnetically coupled to an inductor coil located externally of the patient's body; and wherein the ultrasonic transducer is electrically coupled to the inductor coil of the energy translator circuit and is configured to produce an acoustic field based on the electrical signal.

* * * * *